(12) United States Patent
DeLuca et al.

(10) Patent No.: US 8,604,008 B2
(45) Date of Patent: *Dec. 10, 2013

(54) 2-METHYLENE-19,21-DINOR-1α-HYDROXY-BISHOMOPREGNACALCIFEROL

(75) Inventors: Hector F. DeLuca, Deerfield, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 329 days.

This patent is subject to a terminal disclaimer.

(21) Appl. No.: 11/283,541

(22) Filed: Nov. 18, 2005

(65) Prior Publication Data
US 2006/0135800 A1    Jun. 22, 2006

Related U.S. Application Data (60) Provisional application No. 60/629,958, filed on Nov. 22, 2004.

(51) Int. Cl.
*A61K 31/59* (2006.01)
*C07C 401/00* (2006.01)

(52) U.S. Cl.
USPC ............................. 514/167; 552/653

(58) Field of Classification Search
USPC ............................. 514/167; 552/653
See application file for complete search history.

(56) References Cited

U.S. PATENT DOCUMENTS

| 4,666,634 A | 5/1987 | Miyamoto et al. |
| 5,086,191 A | 2/1992 | DeLuca et al. |

(Continued)

FOREIGN PATENT DOCUMENTS

| EP | 0503923 | 9/1992 |
| JP | 2001-504135 | 3/2001 |

(Continued)

OTHER PUBLICATIONS

Baggiolini, et al., "Stereocontrolled Total Synthesis of 1α,25-Dihydroxycholecalciferol and 1α,25-Dihydroxyergocalciferol," J. Org. Chem. 51, 3098 (1986).

(Continued)

*Primary Examiner* — Sabiha Qazi
(74) *Attorney, Agent, or Firm* — Foley & Lardner LLP (57) ABSTRACT

Compounds of formula I are provided where $X^1$ and $X^2$ are independently selected from H or hydroxy protecting groups. Such compounds may be used in preparing pharmaceutical compositions and are useful in treating a variety of biological conditions.

I

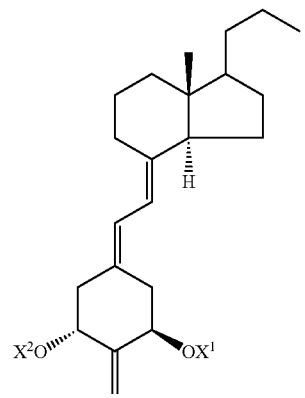

19 Claims, 7 Drawing Sheets

HL-60 Cell Differentiation $EC_{50}$: $1,25(OH)_2D_3 = 2.3 \times 10^{-9}$ M
19,21-dinor = $6.6 \times 10^{-8}$ M

(56) References Cited

U.S. PATENT DOCUMENTS

| | | | |
|---|---|---|---|
| 5,536,713 | A | 7/1996 | Deluca et al. |
| 5,585,369 | A | 12/1996 | DeLuca et al. |
| 5,843,928 | A | 12/1998 | Deluca et al. |
| 5,891,865 | A | 4/1999 | DeLuca et al. |
| 5,936,105 | A | 8/1999 | Paaren |
| 5,936,133 | A | 8/1999 | DeLuca et al. |
| 5,945,410 | A | 8/1999 | DeLuca et al. |
| 6,127,559 | A | 10/2000 | DeLuca et al. |
| 6,392,071 | B1 | 5/2002 | DeLuca et al. |
| 6,440,953 | B1 | 8/2002 | DeLuca et al. |
| 6,537,981 | B2 | 3/2003 | DeLuca et al. |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 6,835,723 | B2 | 12/2004 | DeLuca et al. |
| 6,887,860 | B2 | 5/2005 | DeLuca et al. |
| 7,241,751 | B2 | 7/2007 | DeLuca et al. |
| 7,534,778 | B2 | 5/2009 | DeLuca et al. |
| 7,541,348 | B2 | 6/2009 | DeLuca et al. |
| 7,718,637 | B2 | 5/2010 | DeLuca et al. |
| 7,718,638 | B2 | 5/2010 | DeLuca et al. |
| RE41,491 | E | 8/2010 | DeLuca et al. |
| 2004/0220418 | A1 | 11/2004 | DeLuca et al. |
| 2005/0119242 | A1* | 6/2005 | DeLuca et al. ............... 514/167 |
| 2006/0135799 | A1 | 6/2006 | DeLuca et al. |
| 2006/0135800 | A1 | 6/2006 | DeLuca et al. |
| 2007/0254857 | A1 | 11/2007 | DeLuca et al. |

FOREIGN PATENT DOCUMENTS

| | | |
|---|---|---|
| WO | WO98/41501 | 9/1998 |
| WO | WO-02/20021 | 3/2002 |
| WO | WO-03/051828 | 6/2003 |
| WO | WO-03/075932 | 9/2003 |
| WO | WO2005/051323 | 6/2005 |

OTHER PUBLICATIONS

Daniewski, et al., "A Novel Silylcopper Catalyst for the Reductive Bromination of Hajos Dione. Improved Preparation of a CD Synthon for the Synthesis of Vitamin D," J. Org. Chem. 66, 626-628 (2001).

Mascareñas, et al., "Studies of the Synthesis of Side-Chain Hydroxylated Metabolites of Vitamin D. 3. Synthesis of 25-Ketovitamin $D_3$ and 25-Hydroxyvitamin $D_3$" J. Org. Chem. 51, 1269 (1986).

Posner, et al., "2-Fluoroalkyl A-Ring Analogs of 1,25-Dihydroxyvitamin $D_3$-Stereocontrolled Total Synthesis via Intramolecular and Intermolecular Diels-Alder Cycloadditions. Preliminary Biological Testing," J. Org. Chem. 60, 4617 (1995).

Lythgoe, et al., "Calciferol and its Relatives. Part 22. A Direct Total Synthesis of Vitamin $D_2$ and Vitamin $D_3$," J. Chem. Soc. Perkin Trans. I, N6, 590 (1978).

Lythgoe, "Synthetic Approaches to Vitamin D and its Relatives," Chem. Soc. Rev. 9, 449 (1983).

Mincione, et al., "Improved Conversion of Vitamin $D_2$ into the Windaus Ketone and its Regioselective Hydroxylation via Organoboranes at $C_{25}$," Synth. Commun 19, 723 (1989).

Miyamoto, et al., "Synthetic Studies of Vitamin D Analogues. XIV. Synthesis and Calcium Regulating Activity of Vitamin $D_3$ Analogues Bearing a Hydroxyalkoxy Group at the 2β—Position," Chem. Pharm. Bull. 41(6), 1111 (1993).

Nishii, et al., "The Development of Vitamin $D_3$ Analogues for the Treatment of Osteoporosis," Osteoporosis Int. Suppl. 1, 190 (1993).

Okano, et al., "Regulatory Activities of 2β-(3-Hydroxypropoxy)—1α, 25-Dihydroxy-Vitamin $D_3$, a Novel Synthetic Vitamin $D_3$ Derivative, on Calcium Metabolism," Biochem. Biophys. Res. Commun. 163(3), 1444 (1989).

Ostrem, et al., "24-and 26-homo-1,25-dihydroxyvitamin $D_3$: Preferential activity in inducing differentiation of human leukemia cells HL-60 in vitro," Proc. Natl. Acad. Sci. USA, 84, 2610 (1987).

Perlman, et al., "1α, 25-Dihydroxy-19-Nor-Vitamin $D_3$, a Novel Vitamin D-related Compound with Potential Therapeutic Activity," Tetrahedron Lett. 31(13), 1823 (1990).

Perlman et al., "Novel Synthesis of 19-Nor-Vitamin D Compounds," Tetrahedron Lett. 32(52), 7663 (1991).

Peterson, et al., "Studies of the Ketone Obtained from the Ozonolysis of Vitamin D. Molecular Mechanics Calculations for It and Related Hydrindanones," J. Org. Chem. 51, 1948 (1986).

Posner, et al., "Stereocontrolled Total Synthesis of Calcitriol Derivatives: 1,25-Dihydroxy-2-(4'-hydroxybutyl)vitamin $D_3$ Analogs of an Osteoporosis Drug," J. Org. Chem. 59, 7855 (1994).

Sardina, et al., "Studies on the Synthesis of Side-Chain Hydroxylated Metabolites of Vitamin D. 2. Stereocontrolled Synthesis of 25-Hydroxyvitamin $D_2$," J. Org. Chem. 51, 1264 (1986).

Sicinski, R.R., et al., "New 1α,25-Dihydroxy-19-norvitamin $D_3$ Compounds of High Biological Activity: Synthesis and Biological Evaluation of 2-Hydroxymethyl, 2-Methyl, and 2-Methylene Analogues," J. Med. Chem., 41, 4662-4674 (1998).

Toh et al., "Studies on a Convergent Route to Side-Chain Analogues of Vitamin D: 25-Hydroxy-23-oxavitamin $D_3$," J. Org. Chem. 48, 1414 (1983).

Hekutaa, Efu Deruuka et al., "Cell differentiation-inducing agents containing secosterols", XP002573281, retrieved from STN Database accession No. 1994;153700 *abstract* & JP 05 238937 A, Wisconsin Alumni Research Foundation, Japan, Sep. 17, 1993.

Supplementary European Search Report for EP 05851832.5, dated Apr. 7, 2010.

Office Action for Japanese Pat. Appln. No. 2007-543289, including English translation, dated Nov. 7, 2011, 5 pp.

Office Action for Japanese Pat. Appln. No. 2007-543291, including English translation, dated Nov. 7, 2011, 5 pp.

Communication Pursuant to Article 94(3) EPC for EPO Appln. No. 05848203.5 dated Jan. 20, 2010.

European Search Report for EP0 Appln. No. 05848203.5 dated Sep. 28, 2009.0

Office Action on U.S. Appl. No. 11/282,972 dated Dec, 8, 2009.

Plum, Lori A. et al., "Biologically active noncalcemic analogs of 1alpha, 25-dihydroxyvitamin D with an abbreviated side chain containing no hydroxyl" Proceedings of the National Academy of Sciences of USA, May 4, 2004, pp. 6900-6904, vol. 101, No. 18.

Vanhooke, Janeen L. et al: "Molecular structure of the rat vitamin D receptor ligand binding domain complexed with 2-carbon-substituted vitamin D3 hormone analogues and a LXXLL-containing coactivator peptide", Biochemistry, Mar. 10, 2004, pp. 4101-4110, vol. 43, No. 14, American Chemical Society.

Notice of Allowance for U.S. Appl. No. 11/282,972, mailed on Mar. 30, 2012, 12 pp.

International Search Report dated May 22, 2006 for PCT/US2005/041888.

International Search Report dated May 25, 2006 for PCT/US2005/041886.

International Search Report dated May 25, 2006 for PCT/US2005/041887.

Examiner's First Report for Australian Pat. Appln. No. 2005309820, dated Aug. 31, 2010.

U.S. Final Office Action for U.S. Appl. No. 11/282,972, dated Aug. 26, 2010 and received on Aug. 30, 2010.

Non-Final Office Action for U.S. Appl. No. 11/282,304, mailed on Oct. 17, 2006, 14 pp.

Non-Office Action for U.S. Appln. No. 11/282,972, mailed on Oct. 17, 2006, 10 pp.

Supplementary European Search Report for EPO Pat. Appln. No. 05849207.5, mailed on Sep. 16, 2009, 7 pp.

Written Opinion of the International Searching Authority for Intl. Pat. Appln. No. PCT/US2005/041887, mailed on May 25, 2006, 3 pp.

Written Opinion of the International Searching Authority for Intl. Pat. Appln. No. PCT/US2005/041886, mailed on May 25, 2006, 3 pp.

Written Opinion of the International Searching Authority for Intl. Pat. Appln. No. PCT/US2005/041888, mailed on May 22, 2006, 3 pp.

* cited by examiner

FIGURE 6

2-METHYLENE-19,21-DINOR-1α-HYDROXY-BISHOMOPREGNACALCIFEROL

CROSS REFERENCES TO RELATED APPLICATIONS

This application claims priority to U.S. Provisional Application No. 60/629,958, filed Nov. 22, 2004, the entire disclosure of which is hereby incorporated by reference and for all purposes in its entirety as if fully set forth herein.

FIELD OF THE INVENTION

This invention relates to vitamin D compounds, and more particularly to 2-methylene-19,21-dinor-1α-hydroxy-bishomopregnacalciferol and to pharmaceutical formulations that include this compound. The invention also relates to the use of 2-methylene-19,21-dinor-1α-hydroxy-bishomopregnacalciferol or salts thereof in the preparation of medicaments for use in treating various diseases.

BACKGROUND OF THE INVENTION

The natural hormone, 1α,25-dihydroxyvitamin $D_3$ (also referred to as 1α,25-dihydroxycholecalciferol and calcitriol) and its analog in the ergosterol series, i.e. 1α,25-dihydroxyvitamin $D_2$, are known to be highly potent regulators of calcium homeostasis in animals and humans, and their activity in cellular differentiation has also been established, Ostrem et al., *Proc. Natl. Acad. Sci. USA*, 84, 2610 (1987). Many structural analogs of these metabolites have been prepared and tested, including 1α-hydroxyvitamin $D_3$, 1α-hydroxyvitamin-$D_2$, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1α,25-dihydroxyvitamin $D_3$ and the numbering system used to denote the carbon atoms in this compound are shown below.

1α,25-Dihydroxyvitamin $D_3$=1α,25-Dihydroxycholecalciferol=Calcitriol

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., *Tetrahedron Lett.* 31, 1823 (1990); Perlman et al., *Tetrahedron Lett* 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by the Chugai group as potential drugs for osteoporosis and as antitumor agents. See also Okano et al., *Biochem. Biophys. Res. Commun.* 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., *Chem. Pharm. Bull.* 41, 1111 (1993); Nishii et al., *Osteoporosis Int Suppl.* 1, 190 (1993); Posner et al., *J. Org. Chem.* 59, 7855 (1994), and *J. Org. Chem.* 60, 4617 (1995)).

Various 2-substituted analogs of 1α,25-dihydroxy-19-nor-vitamin $D_3$ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-Hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The invention provides 2-methylene-19,21-dinor-1α-hydroxy-bishomopregnacalciferol and related compounds, pharmaceutical formulations that include 2-methylene-19,21-dinor-1α-hydroxy-bishomopregnacalciferol, and the use of this compound in the preparation of medicaments for use in treating various disease states.

Therefore, in one aspect, the invention provides a compound having the formula I shown below

I where $X^1$ and $X^2$ may be the same or different and are independently selected from H or hydroxy-protecting groups. In some embodiments, $X^1$ and $X^2$ are both hydroxy protecting groups such as silyl groups. In some such embodiments, $X^1$ and $X^2$ are both t-butyldimethylsilyl groups. In other embodiments, $X^1$ and $X^2$ are both H such that the compound is 2-methylene-19,21-dinor-1α-hydroxy-bishomopregnacalciferol having the formula IA as shown below:

IA

In some such embodiments, the compound of formula IA is a compound of formula IB and has the structure shown below:

IB

The above compound exhibits a desired, and highly advantageous, pattern of biological activity. This compound is characterized by relatively high binding to vitamin D receptors, but very low intestinal calcium transport activity, as compared to that of 1α,25-dihydroxyvitamin $D_3$, and has very low ability to mobilize calcium from bone, as compared to 1α,25-dihydroxyvitamin $D_3$. Hence, this compound can be characterized as having little, if any, calcemic activity. Thus, it may be useful as a therapy for suppression of secondary hyperparathyroidism of renal osteodystrophy.

The compound of the invention is also especially suited for treatment and prophylaxis of human disorders which are characterized by an imbalance in the immune system, e.g. in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound of the invention.

The above compound is also characterized by relatively high cell differentiation activity. Thus, this compound also provides a therapeutic agent for the treatment of psoriasis, or as an anti-cancer agent, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compounds of the invention may be used to prepare pharmaceutical formulations or medicaments that include a compound of the invention in combination with a pharmaceutically acceptable carrier. Such pharmaceutical formulations and medicaments may be used to treat various biological disorders such as those described herein. Methods for treating such disorders typically include administering an effective amount of the compound or an appropriate amount of a pharmaceutical formulation or a medicament that includes the compound to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compound may be present in a composition to treat the above-noted diseases and disorders in an amount from about 0.01 μg/gm to about 1 mg/gm of the composition, preferably from about 0.1 μg/gm to about 500 μg/gm of the composition, and may be administered topically, transdermally, orally, or parenterally in dosages of from about 0.01 μg/day to about 1 mg/day, preferably from about 0.1 μg/day to about 500 μg/day.

Further objects, features and advantages of the invention will be apparent from the following detailed description and drawings.

BRIEF DESCRIPTION OF THE DRAWINGS

FIGS. 1-7 illustrate various biological activities of 2-methylene-19,21-dinor-1α-hydroxy-bishomopregnacalciferol (referred to as "19,21-dinor" in the Figures) compared with those of the native hormone 1α,25-dihydroxyvitamin $D_3$ (referred to as "1,25(OH)$_2$D$_3$" in the Figures).

DETAILED DESCRIPTION OF THE INVENTION

2-Methylene-19,21-dinor-1α-hydroxy-bishomopregnacalciferol was synthesized, and tested, and found to be useful in treating a variety of biological conditions as described herein. Structurally, this compound has the formula IA as shown below:

IA

Preparation of 2-methylene-19,21-dinor-1α-hydroxy-bishomopregnacalciferol can be accomplished by condensing an appropriate bicyclic Windaus-Grundmann type ketone (II) with the allylic phosphine oxide III followed by deprotection (removal of the $Y_1$ and $Y_2$ groups).

II

-continued

III

In phosphine oxide III, $Y_1$ and $Y_2$ are preferably hydroxy-protecting groups such as silyl protecting groups. The t-butyldimethylsilyl (TBDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Phosphine oxide III is a convenient reagent that can be used to prepare a large number of 19-nor vitamin D compounds and may be prepared according to the procedures described by Sicinski et al., *J. Med. Chem.,* 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scherme I shows the general procedure for synthesizing phosphine oxide III as outlined in U.S. Pat. No. 5,843,928 which is hereby incorporated by reference in its entirety as if fully set forth herein. Modification of the method shown in Scheme I may be used to produce a large number of vitamin D analogs as will be apparent to those skilled in the art. For example, a wide variety of phosphonium compounds may be used in place of the MePh$_3$P$^+$Br$^-$ used to convert ketone B to alkene C. Examples of such compounds include EtPh$_3$P$^+$Br$^-$, PrPh$_3$P$^+$Br$^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I may be reduced with (Ph$_3$P)$_3$RhCl and H$_2$ to provide other vitamin D analogs. See U.S. Pat. No. 5,945,410 and Sicinski, R. R. et al., *J. Med. Chem.,* 41, 4662-4674 (1998) both of which are hereby incorporated by reference in their entireties and for all purposes. Therefore, the procedure for forming the phosphine oxide shown in Scheme I may be used to prepare a wide variety of vitamin D analogs in addition to the compound of the present invention.

Scheme I

Hydraindanones of structure II can prepared by known methods or adapted methods as will be readily apparent to one of skill in the art and described herein. Specific examples of some important bicyclic ketones used to synthesize vitamin D analogs are those described in Mincione et al., *Synth. Commun* 19, 723, (1989); and Peterson et al., *J. Org. Chem.* 51, 1948, (1986).

An overall process for synthesizing 2-alkylidene-19-nor-vitamin D compounds is illustrated and described in U.S. Pat. No. 5,843,928 which is hereby incorporated by reference in its entirety and for all purposes as if fully set forth herein.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

EXAMPLES

Synthesis of 2-Methylene-19,21-dinor-1α-hydroxy-bishomopregnacalciferol

The synthesis and characteristics of various 19-nor vitamin D analogs is described in numerous United States patents including U.S. Pat. No. 5,843,928, U.S. Pat. No. 6,627,622, U.S. Pat. No. 6,579,861, U.S. Pat. No. 5,086,191, U.S. Pat. No. 5,585,369, and U.S. Pat. No. 6,537,981. Each of the above-described references is hereby incorporated by reference in its entirety and for all purposes as if fully set forth herein.

Compounds of formula I, formula IA, and formula IB were prepared using the methods shown in Schemes I and II. The starting material, compound 1, was prepared using the procedure set forth by Andrzej R. Daniewski and Wen Liu (*J. Org. Chem.* 66, 626-628 (2001) using $Ph_3P^+PrBr^-$ in place of $Ph_3P^+Et\ Br^-$ in the step for converting compound 7 to compound 8 in Scheme I of the article which is hereby incorporated by reference in its entirety and for all purposes as if fully set forth herein. Starting material 1 was then hydrogenated using palladium on carbon as a catalyst to yield the saturated compound 2 having a molecular weight of 196. The reaction was followed using thin layer chromatography (TLC) using a 20% ethyl acetate in a hexane solvent system. Compound 2 was then oxidized with pyridinium chlorochromate as described in U.S. Patent Publication No. 2004/0220418, published on Nov. 4, 2004 (U.S. patent application Ser. No. 10/847,040), hereby incorporated by reference in its entirety and for all purposes as if fully set forth herein, to yield 3 as followed by TLC using the same solvent system. The Ring-A phosphine oxide compound 4 was synthesized as shown in Scheme I. The condensation was carried out again as described in the above-referenced patent documents with n-butyl lithium and was followed by TLC using a solvent of 5% ethyl acetate in hexane to yield compound 5. The t-butyldimethylsilyl protecting groups were removed using tetrabutylammonium fluoride as described in U.S. Patent Publication No. 2004/0220418 to yield compound 6(2-methylene-19,21-dinor-1α-hydroxy-bishomopregnacalciferol). TLC was used to follow completion of the reaction using the solvent system described above. The final product was fully characterized as described below.

Scheme II

2-Methylene-19,21-dinor-1α-hydroxy-bishomopregnacalciferol

UV (in EtOH) $\lambda_{max}$ 244, 252, 262 nm; $^1$H NMR (CDCl$_3$), 0.451 (3H, s, 18-H$_3$), 0.898 (3H, t, J=6.8 Hz, 23-H$_3$), 1.8-2.05 (2H, m), 2.29 (1H, dd, J=13.2, 8.7 Hz, 10α-H), 2.33 (1H, dd, J=13.5, 5.7 Hz, 4β-H), 2.58 (1H, dd, J=13.5, 3.8 Hz, 4α-H), ca. 2.84 (1H, overlapped with 10β-H, 9β-H), 2.86 (1H, dd, J=13.2, 4.5 Hz, 10β-H), 4.49 (2H, m, 1β- and 3α-H), 5.10 and 5.11 (1H and 1H, each s, =CH$_2$), 5.89 and 6.37 (1H and 1H, each d, J=11.4 Hz, 7- and 6-H); MS (APCI) m/z (relative intensity) 331 ([M+H]$^+$, 7), 313 ([M+H]+−H$_2$O, 100), 295 ([M+H]+−2.H$_2$O, 92).

Biological Activity

Vitamin D Receptor Binding

Test Material
Protein Source
Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

PTH Suppression and Hypercalcemia

Species

Adult, female Sprague-Dawley rats were obtained from Harlan (Madison, Wis.).

Animal Husbandry

Upon receipt, the animals were identified by individual tail marks. Animals were housed in suspended, stainless steel, wire-bottom cages. Each cage contained one animal. The animal rooms were maintained at a temperature of 68 to 72° F. and a relative humidity of 25 to 75%. The holding rooms were set to provide 12 hours of light per day. Water and a purified rodent diet (Suda et al., Purified Rodent Diet-Diet 11) containing 0.47% and 0.3% phosphorus and fat soluble vitamins A, D, E and K were provided ad libitum.

Treatment Groups

Animals were randomly assigned to treatment groups (5 animals/group). All doses were administered intraperitoneally in 100 microliters of propylene glycol. Four to seven consecutive doses were given approximately 24 hours apart. Dosing was initiated after the animals had been allowed to acclimate for at least one week.

Dose Preparation
Control Material
A. Negative Control Material

The negative control material was prepared by volumetrically measuring ethanol (<5%) and propylene glycol, mixing, and then placing in storage at 2 to 8° C.

B. Positive Control Material 1,25(OH)$_2$D$_3$ was prepared by determining the concentration of an ethanol stock solution using UV spectrophotometry (extinction coefficient=18,200; $\lambda_{max}$=265 nm). The required amount of 1,25(OH)$_2$D$_3$ was volumetrically measured into propylene glycol so that there was less than 5% ethanol in the final solution. The solution was mixed and then stored at 2 to 8° C.

Test Material

The analogs were prepared by first determining the concentration of an ethanol stock solution using UV spectrophotometry (extinction coefficient=42,000; $\lambda_{max}$=252 nm). The analog solutions were then volumetrically added to propylene glycol so that there was less than 5% ethanol in the final solution. The solution was mixed and stored at 2 to 8° C.

Dose Administration Method

Both control and test articles were administered by intraperitoneal injection in 100 microliters for 4-7 consecutive days spaced approximately 24 hours apart. 1,25(OH)$_2$D$_3$ was given for 4 consecutive days, whereas, the test drugs were given for 7 consecutive days.

Serum PTH Levels

Twenty-four hours after the final dose, blood was collected from the tail artery and the concentration of bioactive serum PTH was measured using the rat BioActive Intact PTH ELISA Kit from Immutopics, Inc. (San Clemente, Calif.).

Serum Calcium Analysis

Twenty-four hours after the final dose, approximately 1 ml of blood was collected from the tail artery of each experimental animal. The blood was allowed to coagulate at room temperature and then centrifuged at 3000×g for 15 minutes. The serum was transferred to a polypropylene tube and stored frozen at −20° C. The level of calcium was determined by diluting the serum into 0.1% lanthum chloride and measuring the absorbance on an atomic absorption spectrophotometer (Perkin Elmer Model 3110, Shelton, Conn.).

Figure 1:
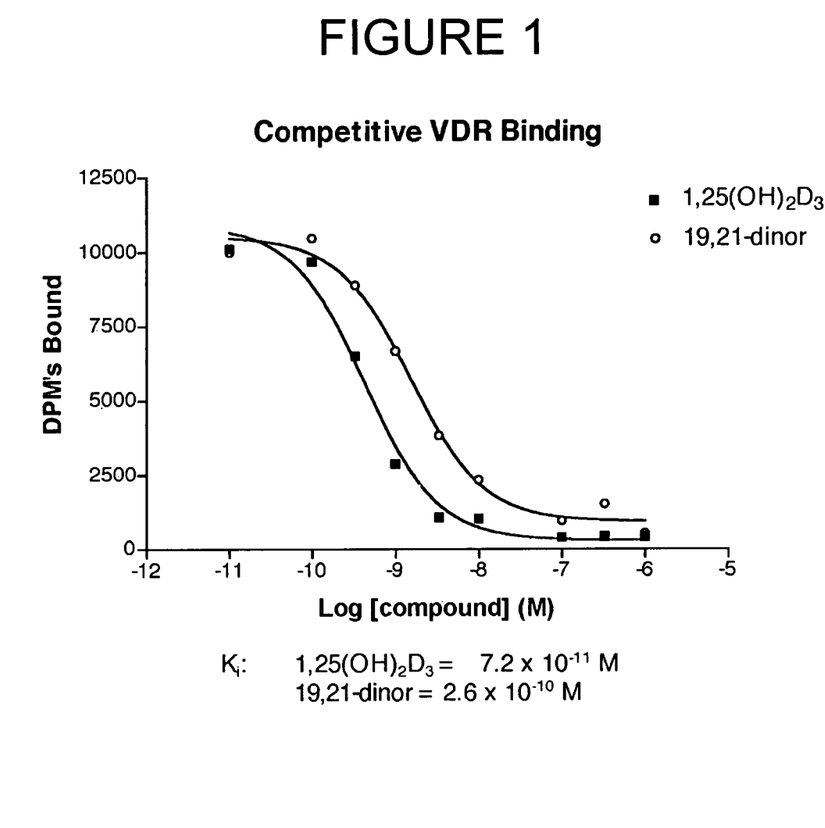
FIG. 1 is a graph comparing the relative activity of 19,21-dinor and 1,25(OH)$_2$D$_3$ to compete for binding with [$^3$H]-1,25-(OH)$_2$-D$_3$ to the full-length recombinant rat vitamin D receptor.
Figure 2:
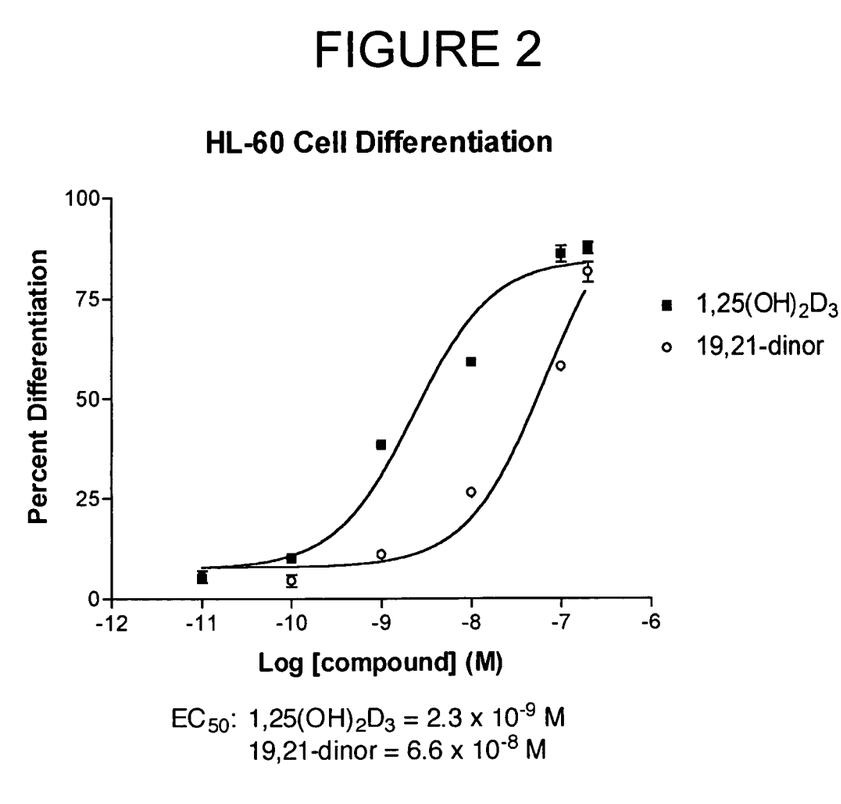
FIG. 2 is a graph comparing the percent HL-60 cell differentiation as a function of the concentration of 19,21-dinor with that of 1,25(OH)$_2$D$_3$.
Figure 3:
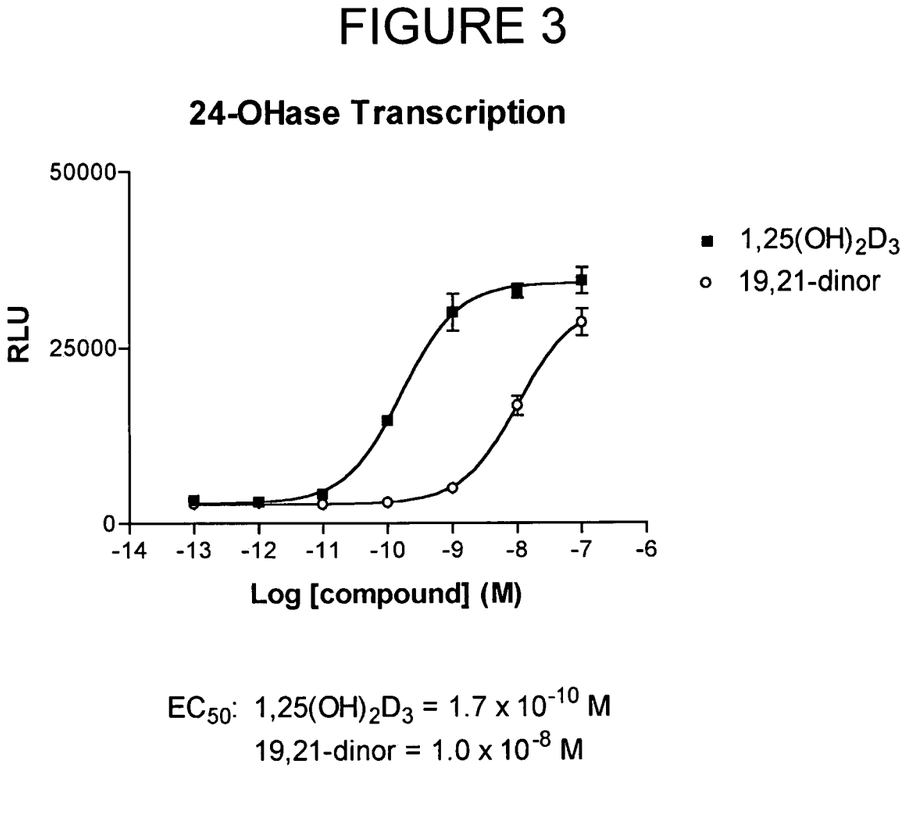
FIG. 3 is a graph comparing the in vitro transcription activity of 19,21-dinor with that of 1,25(OH)$_2$D$_3$.
Figure 4:
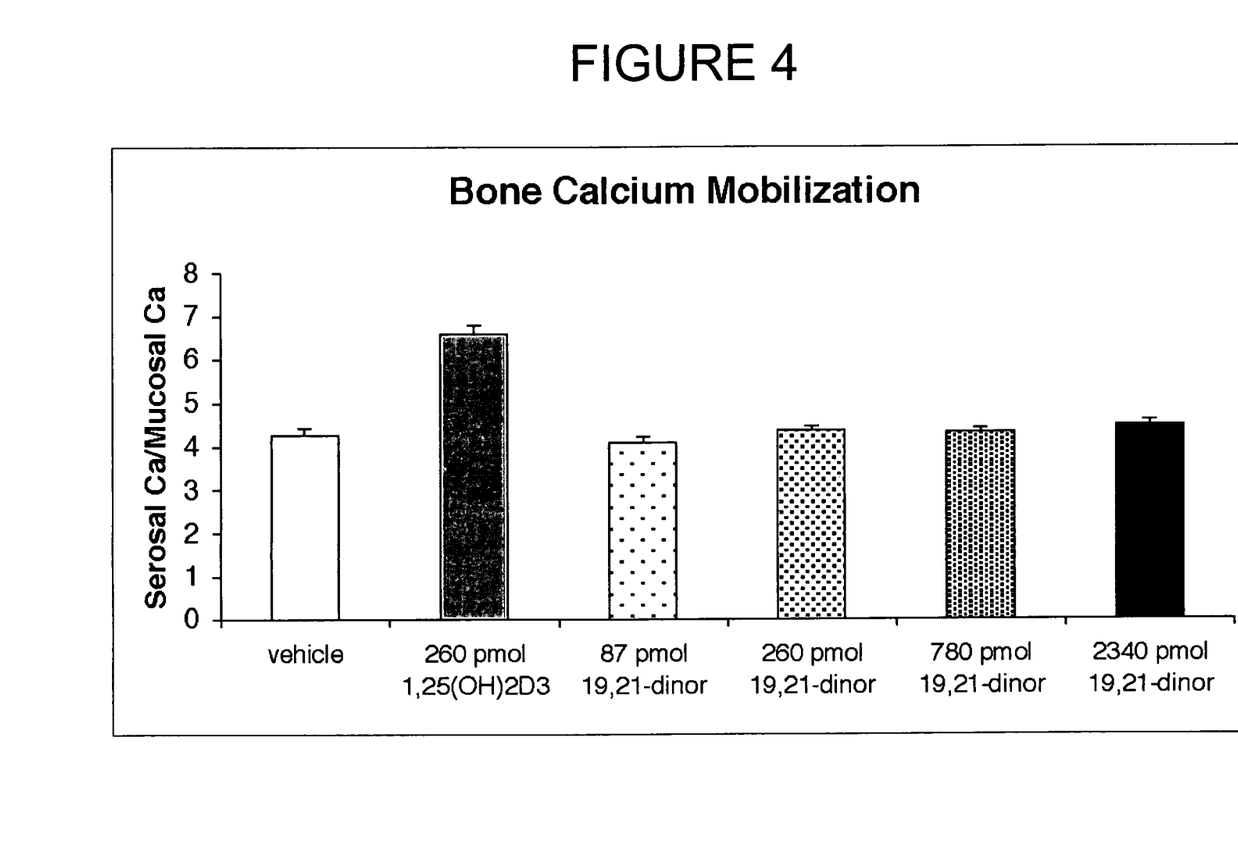
FIG. 4 is a bar graph comparing the bone calcium mobilization activity of 19,21-dinor with that of 1,25(OH)$_2$D$_3$.
Figure 5:
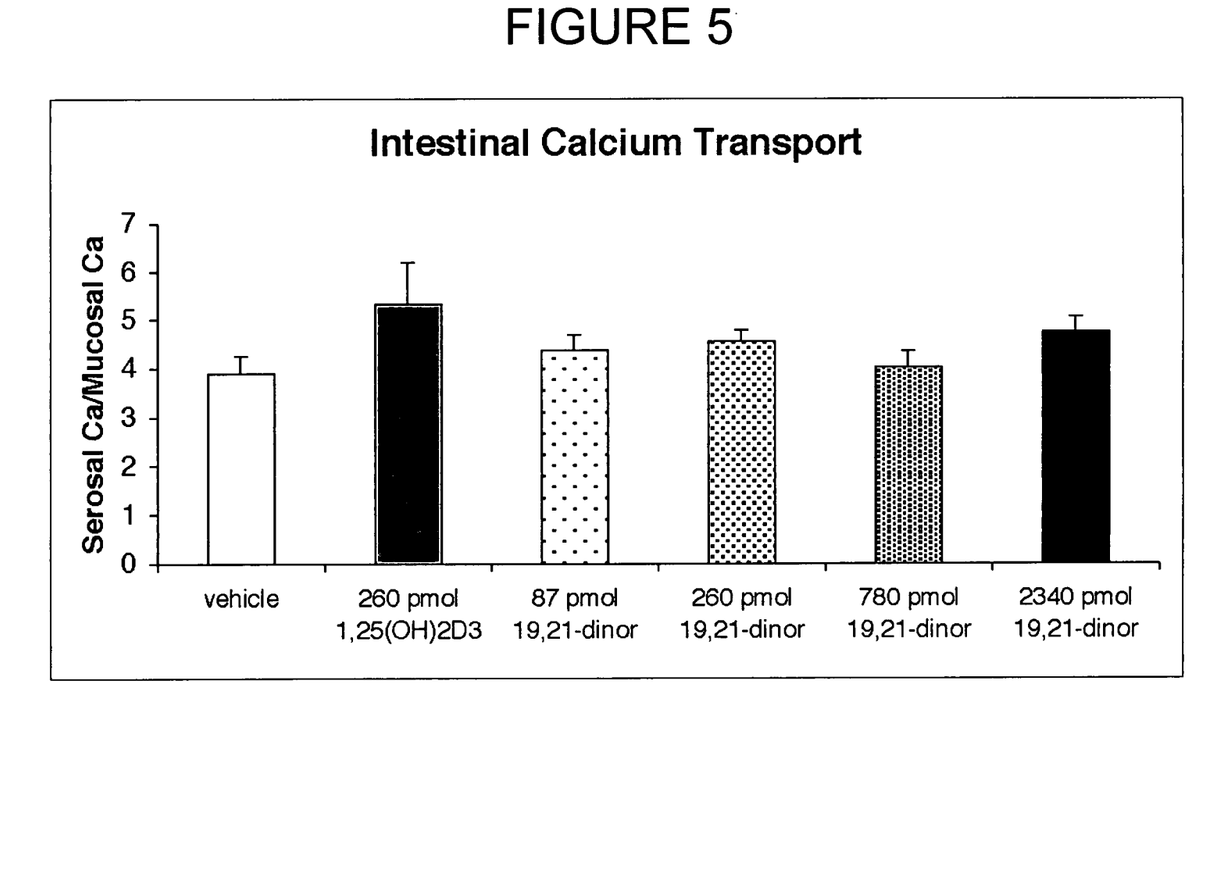
FIG. 5 is a bar graph comparing the intestinal calcium transport activity of 19,21-dinor with that of 1,25(OH)$_2$D$_3$.
Figure 6:
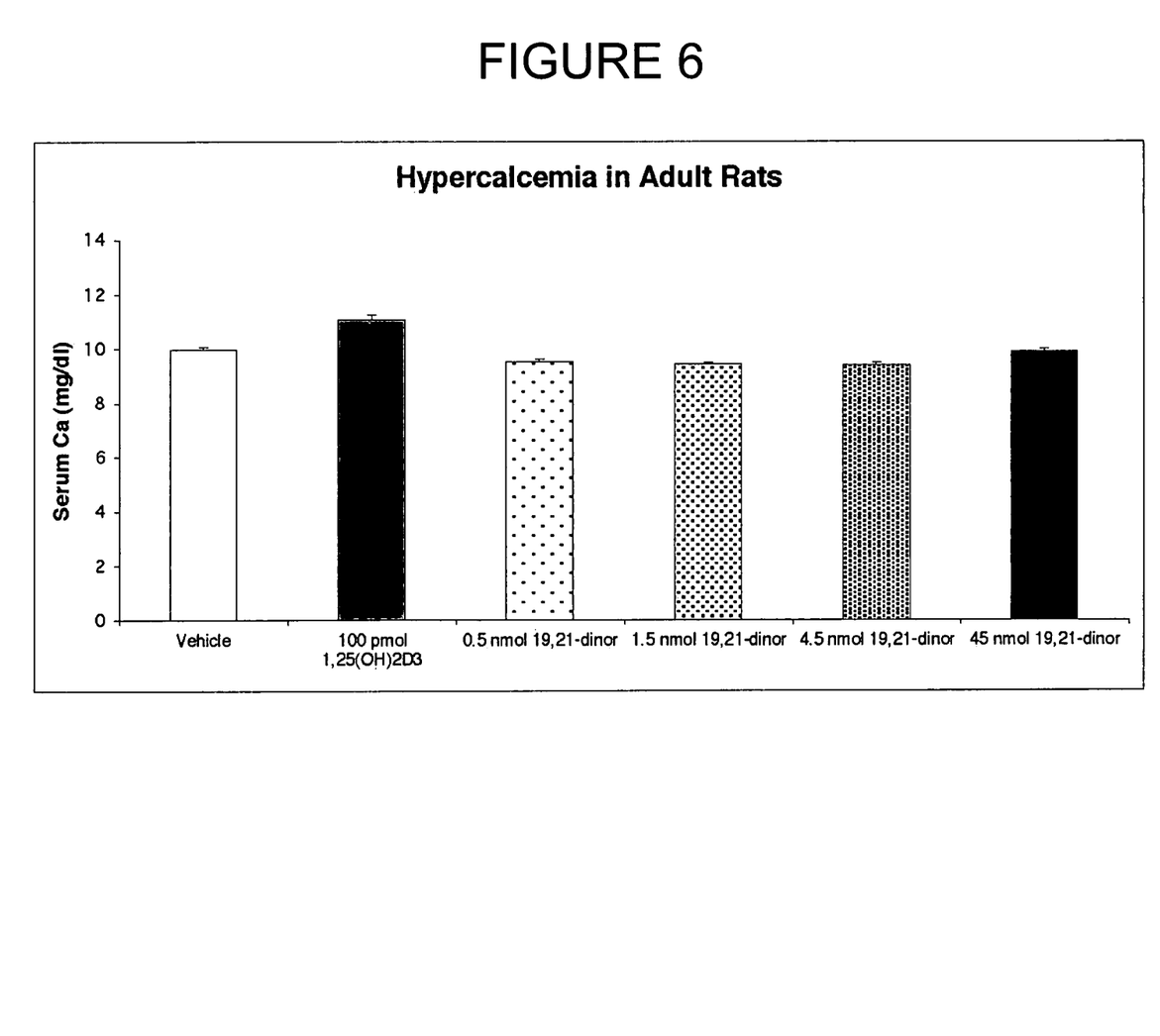
FIG. 6 is a bar graph comparing the serum calcium levels in adult rats after administration of 19,21-dinor and 1,25(OH)$_2$D$_3$.
Figure 7:
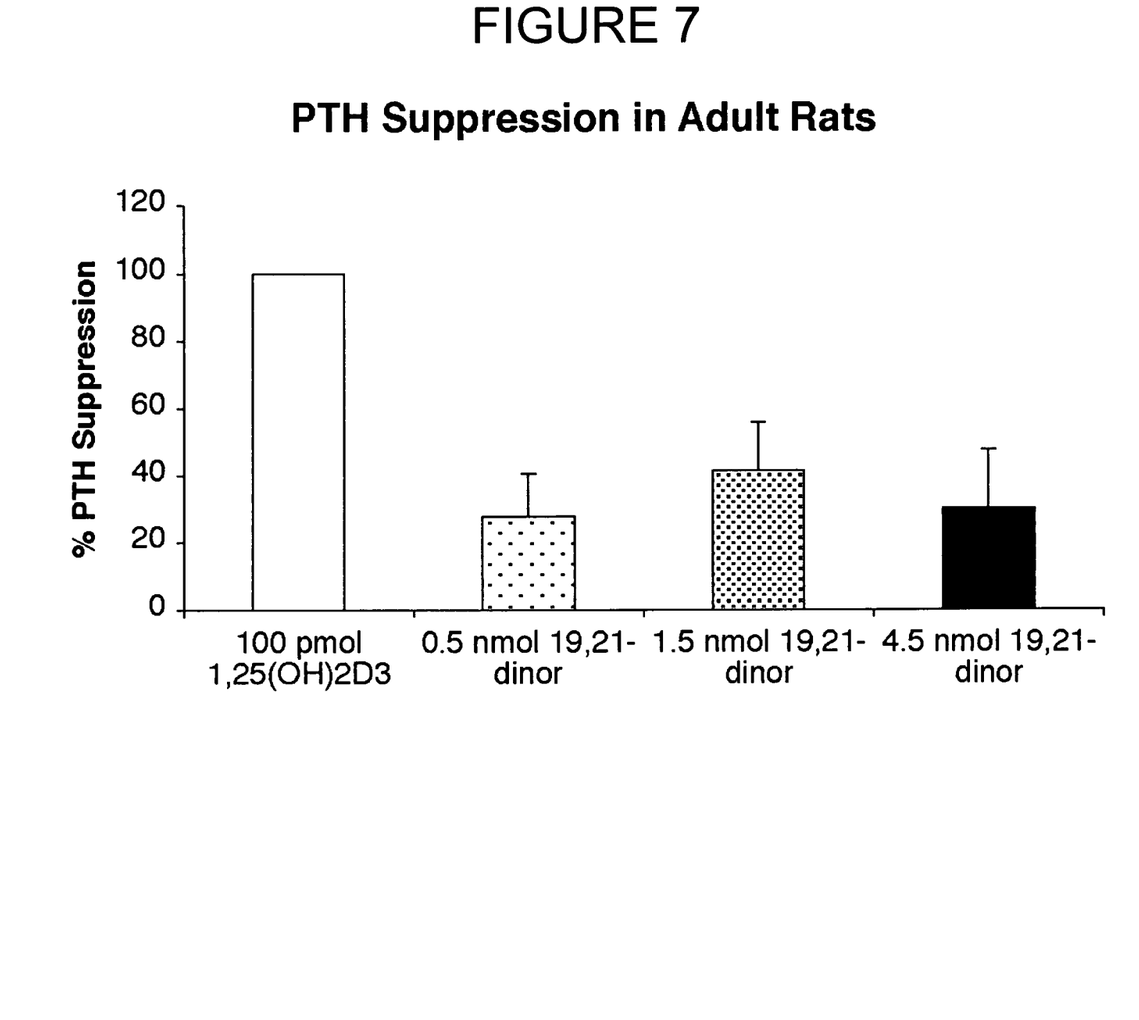
FIG. 7 is a bar graph comparing the percent parathyroid hormone (PTH) suppression in adult rats of 19,21-dinor with 1,25(OH)$_2$D$_3$.

2-Methylene-19,21-dinor-1α-hydroxy-bishomopregnacalciferol binds to the recombinant vitamin D receptor, but is about 5 times less active than is 1α,25-dihydroxyvitamin $D_3$ in this respect (see FIG. 1). Furthermore, it is active in stimulating transcription of a reporter gene stably transfected in Ros17/2.8 (bone) cells, indicating significant biological activity (see FIG. 3). However, it is about 15 times less active than 1α,25-dihydroxyvitamin $D_3$ in inducing differentiation of HL-60 cells (see FIG. 2). It has no calcemic activity when measured either by intestinal calcium transport or bone calcium mobilization even when given at 100 times the dose of 1α,25-dihydroxyvitamin $D_3$ (see FIGS. 4 and 5). However, it does possess significant activity in suppressing parathyroid hormone levels in normal rats (see FIG. 7). This compound should find its uses in the treatment of autoimmune diseases such as multiple sclerosis, type I diabetes, rheumatoid arthritis, lupus, and other similar degenerative diseases. It should also have significant activity in treating malignant growth such as colorectal, breast and prostate cancers. All of these activities should be evident in the absence of raising serum calcium concentrations (see FIG. 6). This compound should also be useful in treating secondary hyperparathyroidism found in patients who have lost kidney function such as those on hemodialysis or peritoneal dialysis.

The compounds of the invention are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and or reducing body fat in animal subject includes administering to the animal subject, an effective amount of the compound or a pharmaceutical composition that includes the compound. Administration of the compound or the pharmaceutical composition to the subject inhibits adipocyte differentiation, inhibits gene transcription, and/or reduces body fat in the animal subject.

For treatment purposes, the compounds defined by formula I, formula IA, and formula IB may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 µg to about 1 mg per day of the compound are appropriate for treatment purposes. In some such embodiments an appropriate and effective dose may range from 0.01 µg to 1 mg per day of the compound. In other such embodiments an appropriate and effective dose may range from 0.1 µg to 500 µg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the invention include an effective amount of 2-methylene-19,21-dinor-1α-hydroxy-bishomopregnacalciferol as the active ingredient, and a suitable carrier. An effective amount of the compound for use in accordance with some embodiments of the invention will generally be a dosage amount such as those described herein, and may be administered topically, transdermally, orally, nasally, rectally, or parenterally.

The compounds of formula IA and IB, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compound may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A compound have the formula I

I wherein $X^1$ and $X^2$ are independently selected from H and hydroxy protecting groups.

2. The compound of claim 1, wherein $X^1$ and $X^2$ are both hydroxy protecting groups.

3. The compound of claim 2, wherein $X^1$ and $X^2$ are both t-butyldimethylsilyl groups.

4. The compound of claim 1, wherein $X^1$ and $X^2$ are both H and the compound has the formula IA

IA

5. A pharmaceutical composition, comprising an effective amount of the compound of claim 4 and a pharmaceutically acceptable carrier.

6. The pharmaceutical composition of claim 5 wherein the effective amount comprises from about 0.01 μg to about 1 mg of the compound per gram of the composition.

7. The pharmaceutical composition of claim 5 wherein the effective amount comprises from about 0.1 μg to about 500 μg of the compound per gram of the composition.

8. A method of treating a subject suffering from a biological condition, comprising administering an effective amount of the compound of claim 4 to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

9. The method of claim 8, wherein the biological condition is psoriasis.

10. The method of claim 8, wherein the biological condition is selected from leukemia, colon cancer, breast cancer, or prostate cancer.

11. The method of claim 8, wherein the biological condition is selected from multiple sclerosis, lupus, diabetes mellitus host versus graft reaction, or rejection of organ transplants.

12. The method of claim 8, wherein the biological condition is selected from rheumatoid arthritis, asthma, or inflammatory bowel diseases selected from celiac disease, ulcerative colitis and Crohn's disease.

13. The method of claim 8, wherein the biological condition is selected from wrinkles, lack of adequate skin firmness, lack of adequate dermal hydration, or insufficient sebum secretion.

14. The method of claim 8, wherein the compound is administered orally to the subject.

15. The method of claim 8, wherein the compound is administered parenterally to the subject.

16. The method of claim 8, wherein the compound is administered transdermally to the subject.

17. The method of claim 8, wherein the compound is administered topically to the subject.

18. The method of claim 8, wherein the compound is administered in a dosage of from 0.01 μg per day to 1 mg per day.

19. The compound of claim 1, wherein $X^1$ and $X^2$ are both H and the compound has the formula IB

IB

* * * * *

UNITED STATES PATENT AND TRADEMARK OFFICE
CERTIFICATE OF CORRECTION

PATENT NO. : 8,604,008 B2
APPLICATION NO. : 11/283541
DATED : December 10, 2013
INVENTOR(S) : Hector F. DeLuca, Lori A. Plum and Margaret Clagett-Dame Page 1 of 1

It is certified that error appears in the above-identified patent and that said Letters Patent is hereby corrected as shown below:

IN THE CLAIMS

Claim 11, Column 16, Line 24

"diabetes mellitus host versus graft reaction," should read "diabetes mellitus, host versus graft reaction,"

Signed and Sealed this
Thirteenth Day of May, 2014

Michelle K. Lee
*Deputy Director of the United States Patent and Trademark Office*